United States Patent [19]

Imai et al.

[11] Patent Number: 5,081,658

[45] Date of Patent: Jan. 14, 1992

[54] METHOD OF MEASURING PLATING AMOUNT AND PLATING FILM COMPOSITION OF PLATED STEEL PLATE AND APPARATUS THEREFOR

[75] Inventors: Kiyotaka Imai; Hiroharu Kato; Tadaaki Hattori; Katsuyuki Nishifuji, all of Tokyo, Japan

[73] Assignee: NKK Corporation, Tokyo, Japan

[21] Appl. No.: 476,251

[22] Filed: Feb. 7, 1990

[30] Foreign Application Priority Data

Mar. 30, 1989 [JP] Japan ................................. 1-79964
Jun. 30, 1989 [JP] Japan ................................. 1-169384

[51] Int. Cl.$^5$ ........................................... G01N 23/223
[52] U.S. Cl. ........................................... 378/45; 378/44; 378/48; 378/53
[58] Field of Search ....................... 378/45, 44, 46, 47, 378/48, 50, 53, 54, 56, 70, 71, 84, 85, 88, 89, 90, 207

[56] References Cited

U.S. PATENT DOCUMENTS 3,703,726  11/1972  Stephenson ............................ 378/48
4,764,945  8/1988  Tadahiro ............................... 378/44

FOREIGN PATENT DOCUMENTS 0036045   4/1981   Japan ................................. 378/45
58-223047 12/1983  Japan .
60-169553  9/1985  Japan .
61-210932  9/1986  Japan .
62-3650    1/1987  Japan .

Primary Examiner—Janice A. Howell
Assistant Examiner—Don Wong
Attorney, Agent, or Firm—Frishauf, Holtz, Goodman & Woodward

[57] ABSTRACT

The plating amount and composition of a plated steel plate are measured by determining a theoretical relation for an intensity at two different light-receiving angles of K-series fluorescent X-rays of analysis target elements reflected by the plate when monochromatized X-rays are radiated onto the plate at two incident angles, measuring a fluorescent X-ray intensity by using standard samples having known plating amounts and compositions, under the same conditions as for obtaining the theoretical relation, and calculating a conversion coefficient for converting the measured value into a theoretical value by the theoretical relation, measuring a fluorescent X-ray intensity obtained from a plated steel plate to be measured having unknown plating amount and composition under the same conditions for obtaining the theoretical relation, and converting the measured fluorescent X-ray intensity into a theoretical intensity by using the conversion coefficient, and calculating a plating amount and composition as parameters in the theoretical relation, which minimize a difference between the theoretical intensity obtained by the theoretical relation and the converted theoretical intensity, as a plating amount and composition of the plate to be measured.

19 Claims, 7 Drawing Sheets

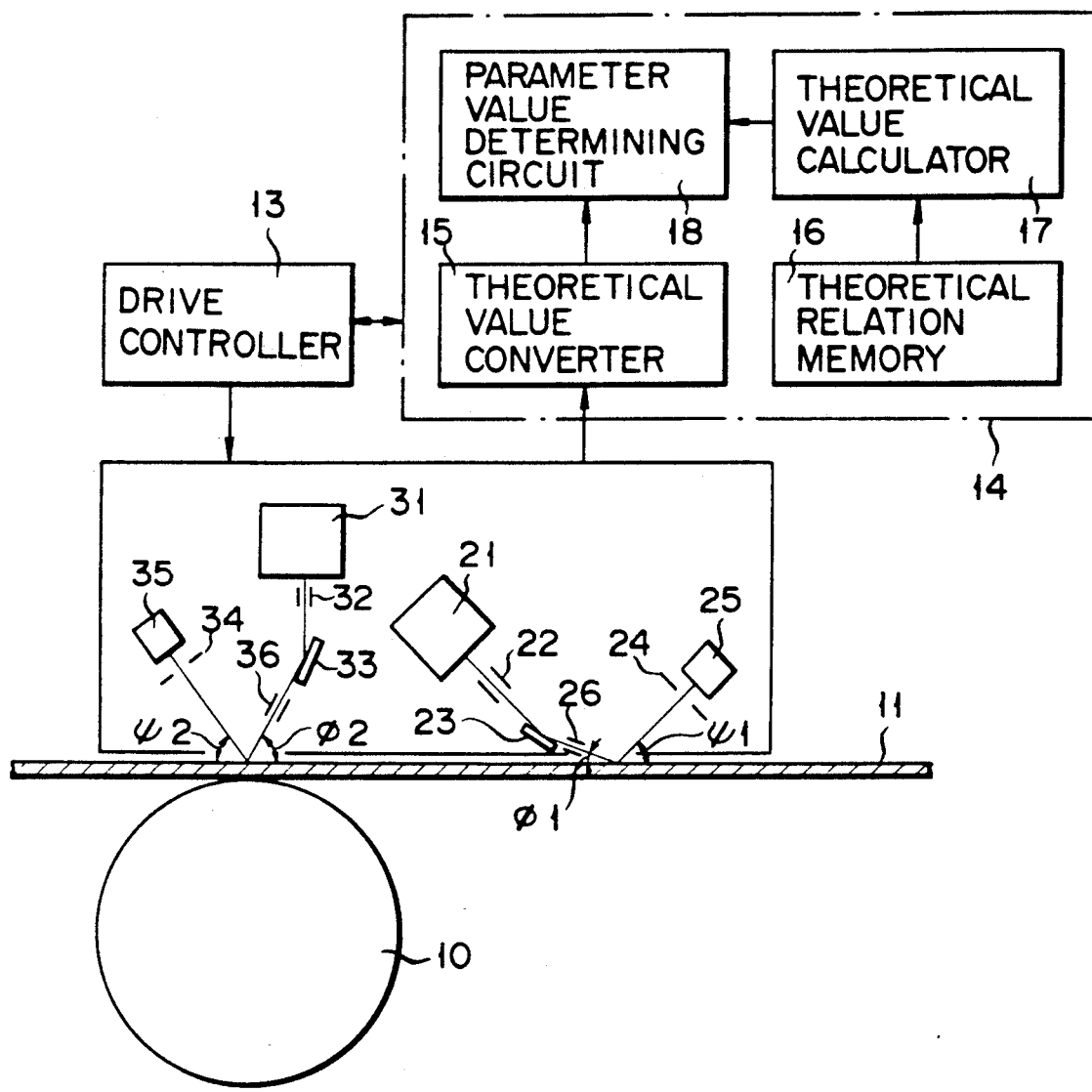
F I G. 3

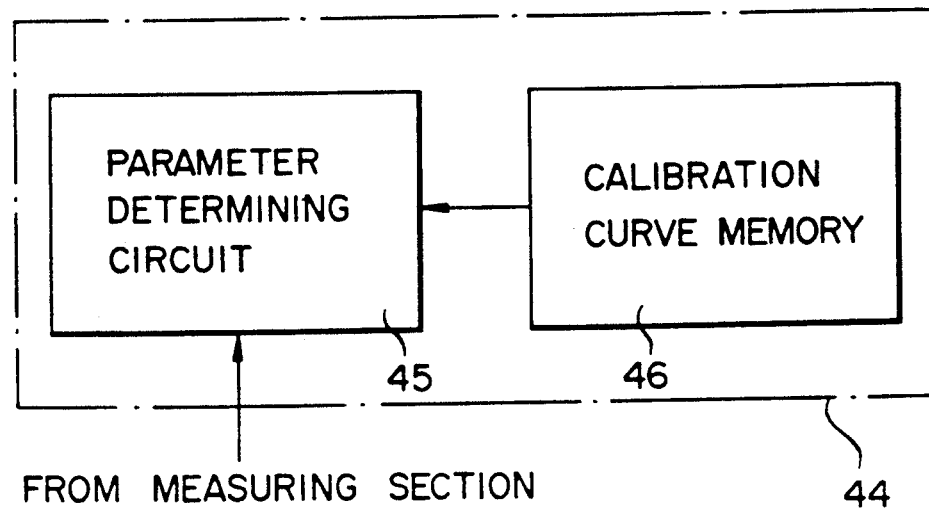
F I G. 6
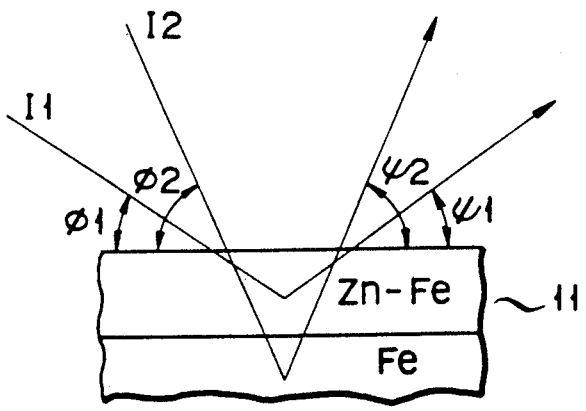
F I G. 7

METHOD OF MEASURING PLATING AMOUNT AND PLATING FILM COMPOSITION OF PLATED STEEL PLATE AND APPARATUS THEREFOR

BACKGROUND OF THE INVENTION

1. Field of the Invention

The present invention relates to a method of measuring a plating amount and a plating film composition of a plated steel plate to be measured by an in-line scheme and a measuring apparatus therefor and, more particularly, to a method of measuring plated steel plate plating amount and plating film composition effective to analyze a portion at which a plating film contains the same component as an underlying metal and a measuring apparatus therefor.

2. Description of the Related Art

One method used to measure a plating amount or a plating film composition of a plated steel plate to be measured, is the fluorescent X-ray analyzinq method. According to this method, after X-rays are radiated onto a steel plate to be measured, the intensity of fluorescent X-rays as a function of the plating thickness and the plating film composition are measured, and the measured value is compared with a calibration curve. In the case of the steel plate having a plating film not containing an underlyinq metal, such as a Zn-plated or Zn-Ni-plated steel plate its plating amount or the plating film composition can be measured by an in-line scheme.

If, however, a plating film of a steel plate contains an underlying metal, as in the case of, for example, a Zn-Fe-alloy-plated steel plate, which has recently attracted attention because of its high corrosion resistance and good workability, measurement of the plating amount and the plating film composition by means of the fluorescent X-ray corresponding to analyzing method has the following disadvantages: Since, when using the fluorescent X-ray analyzing method, it is difficult to distinguish fluorescent X-rays F contained in a plating film from those corresponding to Fe as an underlying metal, it is difficult to obtain an interrelation between the fluorescent X-ray intensity and the plating amount and the plating film composition, and the plating amount and the plating film composition cannot be measured by an in-line scheme.

Consequently, the following two analyzing methods have been proposed with the aim of overcoming the above disadvantages.

One method proposed is an in-line analyzing method (Published Unexamined Japanese Patent Application No. 58-223047) in which so-called white X-rays having a plurality of wavelengths are radiated onto a Zn-Fe-alloy-plated steel plate, and the intensity of a K-series fluorescent X-ray is measured by detectors located at a 1st-measurement-angle position, from which substantially no fluorescent X-rays from a metal underlying the plated steel plate can be detected in terms of depth of X-ray penetration, and at a 2nd-measurement-angle position, from which the fluorescent X-rays from the underlying metal can detected, whereby the plating amount and the plating film composition can be obtained on the basis of both measured values.

The other method is one (Published Unexamined Japanese Patent Application No. 60-169533) in which the plating amount is measured on the basis of diffraction X-rays corresponding to o-Fe of an underlying metal, by way of utilizing the absorption by a plating film of a Zn-Fe-alloy-plated steel plate, and wherein the plating film composition is measured on the basis of the diffraction X-ray intensity of at least one phase selected from a Zn-Fe-alloy phase and an $\eta$ phase in the plating film.

However, in the case of the former of the above two fluorescent X-ray analyzing methods, the following problems arise, due to white X-rays being used as incident X-rays.

(a) Since high-energy X-rays in white X-rays do not attenuate very much in a plating film of a plated steel plate, they therefore can penetrate to a considerable depth. Consequently, the 1st measurement angle must be set to 5 or less in order to ensure that fluorescent X-rays from an underlying metal are not detected. As a result, the measurement distance varies in accordance with variation in the perpendicular direction to the surface of the plated steel plate, the fluorescent X-ray intensity also varying in accordance with variation in the measurement angle, giving rise to a problem of low measurement precision.

(b) The plating amount and the plating film composition may be obtained by comparing a measured intensity obtained by actually radiating X-rays on a plated steel plate, with a theoretical intensity obtained by a known theoretical intensity relation. Since, however, calculation of the theoretical intensity is adversely affected by spectral variation in incident X-rays, caused by, for example, deterioration over time of the X-ray tube, measurement precision is undesirably decreased.

(c) In the case of calculating an analysis value by comparing the measured intensity with the theoretical intensity calculated from the known theoretical intensity relation, the calculation time is prolonged, since wavelength integration must be performed upon calculation of the theoretical intensity. Consequently, the measurement time is increased.

(d) A calibration curve can be used in order to overcome the disadvantage described in item (c) above. Using this method, however, 20 to 30 types of standard sample must be prepared in order to form a model considering a matrix effect, resulting in a very time-consuming troublesome analyzing method.

The latter diffraction X-ray analyzing method has the following drawbacks:

(a) Since the diffraction X-ray intensity corresponding the $\alpha$-Fe of an underlying metal depends on not only the plating amount but also on, for example, the type or thickness of the steel plate, the texture of the steel plate, which changes in accordance with manufacturing conditions of a plated steel plate and the like, and the plating film composition, this gives rise to a problem of measurement precision.

(b) The diffraction X-ray intensity of an alloy phase changes in accordance with plating conditions, and the structure or composition of an alloy differs depending on whether the plating material used is a molten plating material or an electric plating material. Therefore, satisfactory measurement precision can not be obtained.

SUMMARY OF THE INVENTION

The present invention has been developed in consideration of the above situation and has as its object to provide a method of measuring the plating amount and the plating film composition of a plated steel plate, which method is capable of measuring a plating amount and a plating film composition in an in-line scheme while reducing an influence of a variation on the surface profile of a plated steel plate, is capable of improving analysis precision and reducing the analysis time, and is capable of reliably measuring the plating amount and the plating film composition by using a small number of standard samples.

It is another object of the present invention to provide an apparatus for measuring a plating amount and a plating film composition, which apparatus is capable of accurately measuring the plating amount and the plating film composition in an in-line scheme with a simple arrangement.

A method of measuring the plating amount and the plating film composition of a plated steel plate according to the present invention comprises the steps of: (a) determining a theoretical relation or formula for an intensity or intensity ratio at two different light-receiving angles of K-series fluorescent X-rays of analysis target elements reflected by the plated steel plate when monochromatized X-rays or characteristic X-rays are radiated onto the plated steel plate at two different incident angles; (b) measuring a fluorescent X-ray intensity or intensity ratio by using standard samples having known plating amounts and plating film compositions under the same conditions as for obtaining the theoretical relation or formula and calculating a conversion coefficient for converting the measured value into a theoretic value by the theoretical relation or formula; (c) measuring a fluorescent X-ray intensity or intensity ratio obtained from a plated steel plate to be measured having unknown plating amount and plating film composition under the same conditions for obtaining the theoretical relation or formula, and converting the measured fluorescent X-ray intensity or intensity ratio into a theoretical intensity or intensity ratio by using the conversion coefficient; and (d) calculating a plating amount and a plating film composition as parameters in the theoretical relation or formula, which substantially minimize a difference between the theoretical intensity or intensity ratio obtained by the theoretical relation or formula and the converted theoretical intensity or intensity ratio, as a plating amount and a plating film composition of the plated steel plate to be measured.

Another method of measuring a plating amount and a plating film composition of a plated steel plate according to the present invention comprises the steps of: (a) calculating a calibration curve of an intensity or intensity ratio at two different light-receiving angles of K-series fluorescent X-rays of analysis target elements obtained from standard samples having known plating amount and plating film composition when monochromatized X-rays or characteristic X-rays are radiated on the standard samples at two different incident angles; (b) measuring the fluorescent X-ray intensity or intensity ratio obtained from a plated steel plate to be measured having unknown plating amount and plating film composition under the same conditions as for obtaining the calibration curve; and (c) calculating a plating amount and a plating film composition as parameters in the calibration curve, which substantially minimize a difference between the fluorescent X-ray intensity or intensity ratio obtained by the calibration curve and the measured fluorescent X-ray intensity or intensity ratio, as a plating amount and a plating film composition of the plated steel plate to be measured.

An apparatus for measuring a plating amount and a plating film composition of a plated steel plate according to the present invention comprises: (a) X-ray generating means for generating X-rays; (b) converting means for converting X-rays generated by X-ray generating means into monochromatic X-rays or characteristic X-rays; (c) a pair of detectors for receiving, at two different angles, K-series fluorescent X-rays of analysis target elements generated when the monochromatic X-rays or characteristic X-rays are radiated onto a plated steel plate to be measured, and measuring the intensities thereof; (d) a slit system for guiding X-rays generated by the X-ray generating means to the pair of detectors via the converting means and the plated steel plate to be measured; (e) storage means for storing a theoretical relation or formula, using a plating amount and a plating film composition of a plated steel plate as parameters, for calculating a theoretical intensity or intensity ratio of fluorescent X-rays to be obtained in a given measurement system; (f) theoretical value calculating means for calculating a theoretical value of the fluorescent X-ray intensity or intensity ratio by the theoretical relation or formula while changing the parameters; (g) theoretical value converting means for converting an actually measured fluorescent X-ray intensity or intensity ratio into a theoretical intensity or intensity ratio; and (h) plating amount/plating film composition determining means for determining a plating amount and a plating film composition as the parameters, which substantially minimize a difference between the converted theoretical intensity or intensity ratio and the theoretical intensity or intensity ratio obtained by the theoretical relation.

Another apparatus for measuring a plating amount and a plating film composition of a plated steel plate according to the present invention comprises: (a) X-ray generating means for generating X-rays; (b) converting means for converting X-rays generated by the X-ray generating means into monochromatic X-rays or characteristic X-rays; (c) a pair of detectors for receiving, at two different angles, K-series fluorescent X-rays of analysis target elements generated when the monochromatic X-rays or characteristic X-rays are radiated onto a plated steel plate to be measured, and measuring the intensities thereof; (d) a slit system for guiding X-rays generated by the X-ray generating means to the pair of detectors via the converting means and the plated steel plate to be measured; (e) storage means for storing a calibration curve of a theoretical intensity or intensity ratio of fluorescent X-rays to be obtained in a given measurement system with respect to a plating amount and a plating film composition of a plated steel plate; and (f) plating film composition determining means for determining a plating amount and a plating film composition which substantially minimize a difference between an actually measured fluorescent X-ray intensity or intensity ratio and a fluorescent X-ray intensity or intensity ratio obtained by the calibration curve.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

FIG. 3 is a schematic view showing an apparatus for measuring a plating amount and a plating film composition of a plated steel plate according to the first aspect of the present invention;

FIG. 6 is a view showing a modification of a signal processor of the apparatus shown in FIG. 3;

FIG. 7 is an X-ray radiation state according to the second aspect of the present invention;

DETAILED DESCRIPTION OF THE PREFERRED EMBODIMENTS

Embodiments to be presented below have a measuring system satisfying the following conditions in order to perform in-line measurement.

(A) Incident X-rays having a satisfactory fluorescent X-ray intensity can be obtained by using a commercially available X-ray tube.

(B) Measurement angles such as an X-ray incident angle and a fluorescent-X-ray-receiving angle can be realized by an in-line scheme, i.e., 5 or more.

In addition, the intensity of fluorescent X-rays generated from a plated steel plate is measured by a radiation detector, and preferably, a semiconductor detector.

A method of measuring a plating amount and plating film composition according to the first embodiment of the present invention will be described below by taking measurement of a plating amount and a plating film composition (Fe%) of a Zn-Fe-alloy-plated steel plate as an example.

Figure 1:
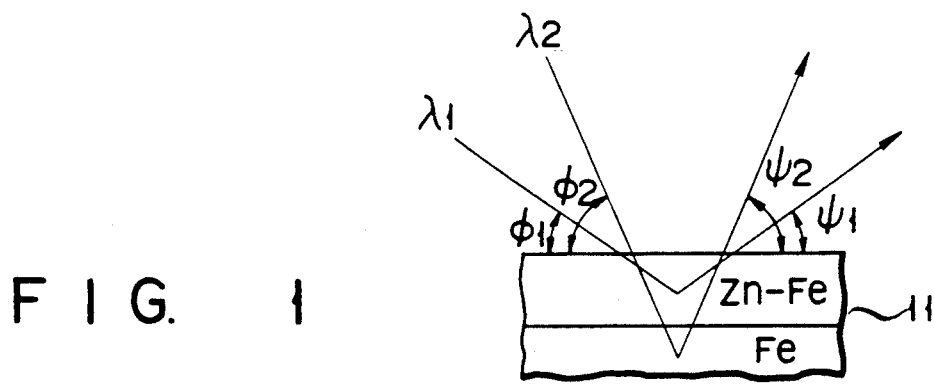
FIG. 1 is a view showing an X-ray radiation state according to the first aspect of the present invention.

FIG. 1 is a view showing an X-ray radiation state for a Zn-Fe-alloy-plated steel plate in order to carry out the method of the present invention. As shown in H 5 FIG. 1, monochromatized X-rays having wavelengths of $\lambda_1$ and $\lambda_2$ are radiated on a plated steel plate 11 to be measured at incident angles of $\phi_1$ and $\phi_2$ and K-series fluorescent X-ray intensities produced by the plate 11, i.e., the intensity of K$\alpha$-rays of Fe and the intensity of K$\lambda$-rays of Zn are measured at light-receiving angles of $\psi_1$ and $\psi_2$.

Figure 2A:
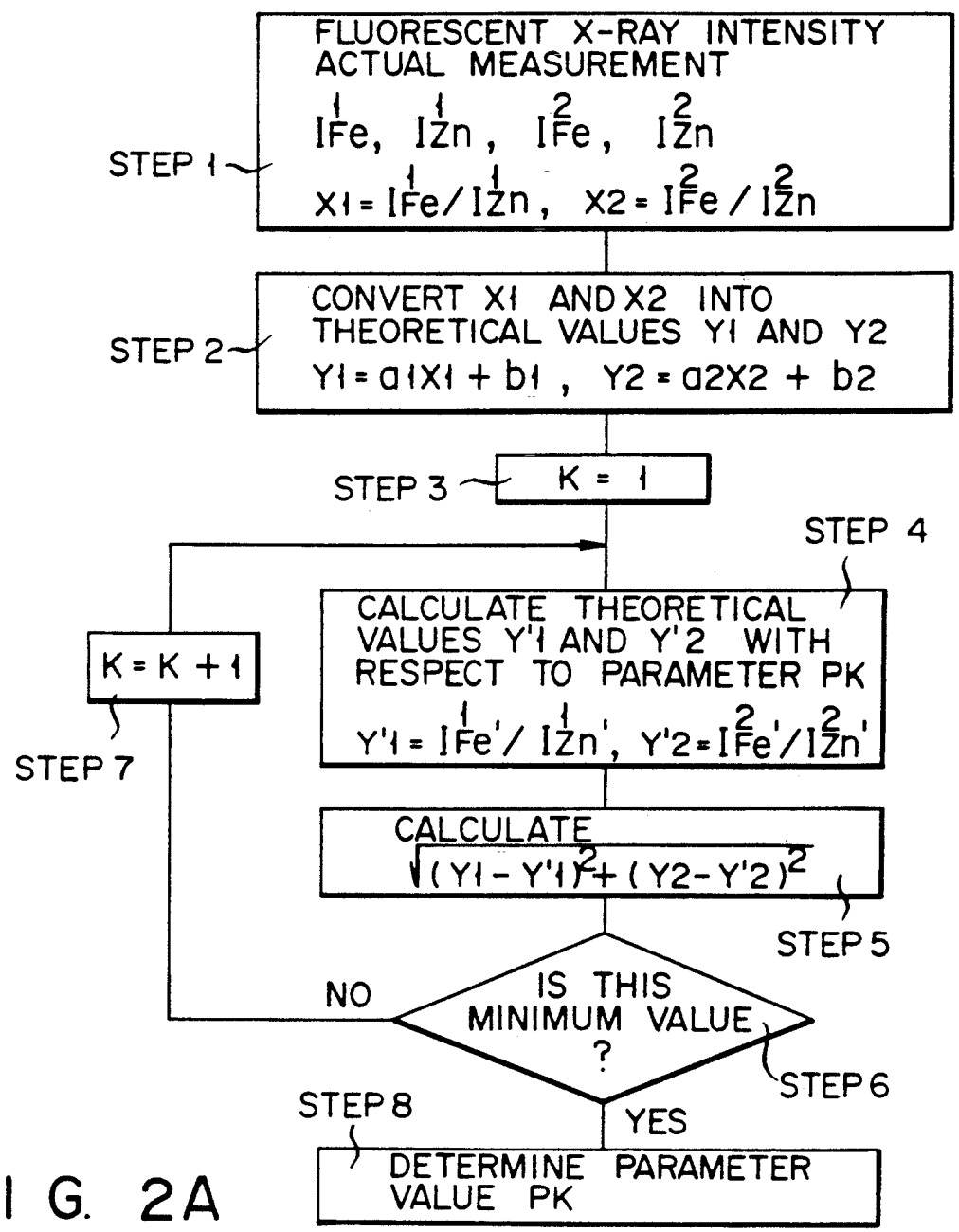
FIGS. 2A and 2B are flow charts for explaining a method of measuring a plating amount and a plating film composition of a plated steel plate according to an embodiment of the present invention, respectively.

In order to carry out this method, as shown in FIG. 2A, the following operations are performed (STEP 1) assuming that an Fe-K$\alpha$ ray intensity and Zn-K$\alpha$ ray intensity measured at the measurement angles ($\phi_1$, $\phi_1$) are $I^1Fe$ and $I^1Zn$, respectively, and an Fe-K$\alpha$ ray intensity and Zn-K$\alpha$ ray intensity measured at the measurement angles ($\phi_2$, $\phi_2$) are $I^2Fe$ and $I^2Zn$, respectively:

$$X_1 = I^1Fe/I^1Zn$$

$$X_2 = I^2Fe/I^2Zn$$

$X_1$ and $X_2$ are converted into theoretical values. In this case, the theoretical values are obtained as values corresponding to $X_1$ and $X_2$ on the basis of values obtained by calculating a fluorescent X-ray intensity measured under the same X-ray wavelength, X-ray intensity, and geometric conditions as actual measurement conditions by a theoretical relation or formula (hereinafter referred to as "theoretical relation") using a plating amount and a plating film composition of a plated steel plate as parameters. An actual measured value differs from the value of the theoretical intensity in accordance with sensitivity characteristics of a detector, an influence of a slit system, and the like.

The measured values $X_1$ and $X_2$ are converted into theoretical values $Y_1$ and $Y_2$, respectively, by the following conversion equations (STEP 2):

$$Y_1 = a_1 X_1 + b_1$$

$$Y_2 = a_2 X_2 + b_2$$

In the above equations, $a_1$, $a_2$, $b_1$, and $b_2$ are conversion coefficients. These conversion coefficients are obtained by measuring a fluorescent X-ray intensity or intensity ratio, under the same conditions as those for obtaining the above theoretical relations, by using a standard sample having known plating amount and plating film composition, and converting the measured value into a theoretical intensity or intensity ratio by using the above theoretical relations. That is, the conversion coefficients a1, $a_2$, $b_1$, and $b_2$ are calculated beforehand by regression analysis or the like so that the values $Y_1$ and $Y_2$ calculated by the theoretical relations by using the plating amount and the plating film composition of the standard sample and the values $X_1$ and $X_2$ calculated from the measured fluorescent X-ray intensity satisfy the above equations.

As described above, since the theoretical relations are used to calibrate a difference with respect to the actual measurement system by using the standard sample, relations of a plating amount and a plating film composition with respect to a fluorescent X-ray intensity or intensity ratio can be obtained by using a small number of standard samples.

After the theoretical values $Y_1$ and $Y_2$ are obtained in STEP 2, $Y'_1$ and $Y'_2$ corresponding to $Y_1$ and $Y_2$ are obtained by an existing fluorescent X-ray intensity relation using a parameter $P_k$ ($k=1$) having a variable plating amount and Fe% (STEP 3 and STEP 4). Thereafter, the following operation is performed (STEP 5):

$$\sqrt{(Y_1-Y'_1)^2+(Y_2-Y'_2)^2}$$

The same operation is performed while the parameter Pk is changed, and the parameter value which substantially minimize the operation value of STEP 5 is determined. In FIG. 2A, whether or not the operation value of STEP 5 is a minimum value is judged (STEP6). If the operation value is not a minimum value, the operation using a next paramount is performed (STEPs 7, 4, and 5). If the operation value is a minimum value, the operation value is determined as the parameter value (STEP8). That is, the operation is proceeded while the parameter Pk is changed, until the above operation value is the minimum value. The parameter value is determined when the minimum value is appeared. This parameter value corresponds to the plating amount and the Fe content. Therefore, the plating amount and the plating film composition of the plated steel plate 11 can be obtained by using the parameter value.

Figure 2B:
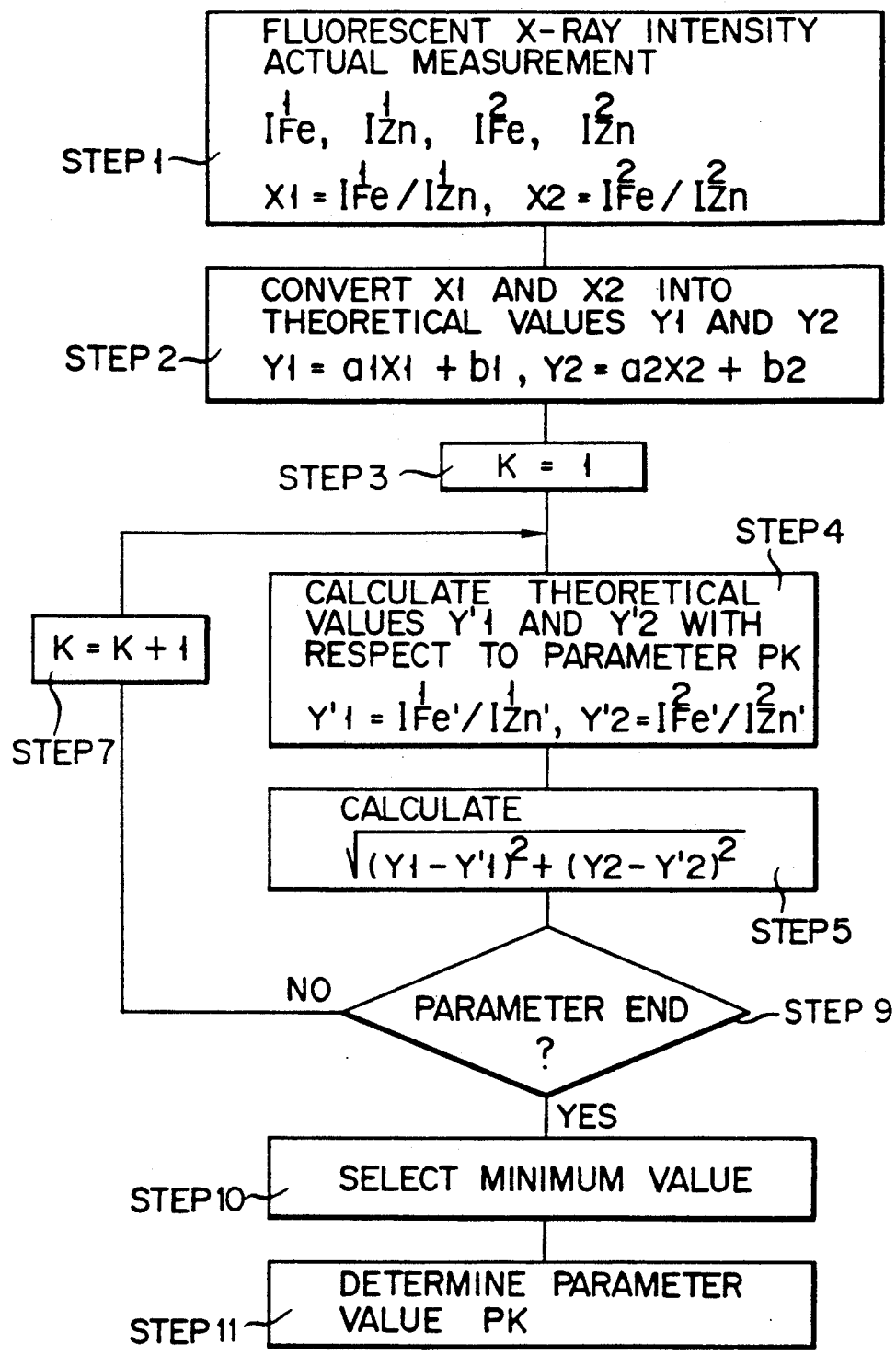

The plating amount and the plating film composition can be measured as is shown in FIG. 2B. In FIG. 2B, the operation of STEP5 is performed by the number of times corresponding to the number of parameters while the plating amount and the value of the parameter Pk is changed (STEPs 9, 7, 4 and 4). The value of the parameter corresponding to the minimum value of the operated values is selected (STEP 10) and determined as a parameter value (STEP 11). This parameter value corresponds to the plating amount and the Fe content. The plating amount and the plating film composition of the plated steel plate 11 can be obtained by using the parameter value.

An analysis result obtained by using the above measuring method corresponding to FIG. 2A will be described in detail below. Assume that $X_1$ measurement conditions are, for example, incident X-ray wavelength $\lambda_1 = 1.26$ Å and measurement angles $(\phi_1, \psi_1) = (15°, 45°)$, and those for $X_2$ are, for example, incident X-ray wavelength $\lambda_2 = 0.71$ Å and measurement angles $(\phi_2, \psi_2) = (75°, 60°)$. Note that by using X-ray tubes having a tungsten target and molybdenum target for $X_1$ and $X_2$, respectively, the wavelength $\lambda_1$ and $\lambda_2$ respectively close to W-I$\beta$ ray and Mo-K$\alpha$ ray can be obtained to satisfy the above condition (A).

Of the two pairs of measurement angles, wavelength $\lambda_1 = 1.26$ Å having a large attenuation amount and a small depth of penetration with respect to a plating film is used for the pair of smaller measurement angles $(\phi_1, \psi_1)$. Therefore, the measurement angles of the pair are 15° and 45°, i.e., satisfy the condition (B) described above. As a result, an influence of a variation in the thickness direction of a plated steel plate on a measurement distance and a measurement angle variation can be reduced.

As a difference in characteristics corresponding to the plating amount and Fe% is increased between $X_1$ and $X_2$, measurement precision is improved. Therefore, an attenuation amount of the wavelength $\lambda_2$ with respect to the plating film is set smaller than that of the wavelength $\lambda_1$, and the measurement angle $(\phi_2, \psi_2)$ is set larger than the measurement angle $(\phi_1, \psi_1)$, thereby increasing the maximum depth capable of detecting fluorescent X-rays, i.e., an analysis depth. In order to decrease the measurement distance variation, it is preferred to decrease the beam size of incident X-rays and to widen the field of view of a detector so that fluorescent X-rays are detected from all portions on which the incident X-rays are radiated regardless of the measurement distance variation. For this purpose, a pinhole collimator having a diameter of 2 to 5 mm is used at the incident side, and the window of a detector at the light-receiving side is opened.

When a large number of standard samples can be used, the relationship of the plating amount and the plating film composition with respect to the fluorescent X-ray intensity or intensity ratio (that is, the calibration curve), which is obtained by the standard samples, may be used instead of the above theoretical relations to obtain a plating amount and a plating film composition of the plated steel plate 11.

An embodiment of an apparatus according to the present invention will be described with reference to FIG. 3. Referring to FIG. 3, reference numeral 11 denotes a plated steel plate to be measured. The plate 11 is guided by a guide roller 10. A measuring system 12 is located above the plate 11. The system 12 comprises: two X-ray tubes 21 and 31 for generating X-rays in predetermined directions; monochromators 23 and 33 for monochromatizing white X-rays incident from the tubes 21 and 31 through collimators 22 and 32, respectively, and guiding the monochromatized rays toward the plate 11 at predetermined incident angles; and detectors 25 and 35 for measuring fluorescent X-ray intensities obtained from the plate 11 through flat-plate slits 24 and 34, respectively. Reference numerals 26 and 36 denote collimators. Note that the collimator 26 is preferably a pinhole collimator in order to reduce influences of variations in measurement distance and measurement angle. The positions of the tubes 21 and 31, the monochromators 23 and 33, the collimators 22, 26, 32, and 36, the detectors 25 and 35, and the slits 24 and 34 can be adjusted by drive control signals from a drive controller 13.

Reference numeral 14 denotes a signal processor comprising: a theoretical value converter 15 for converting a fluorescent X-ray intensity or intensity ratio measured by the two detectors 25 and 35 into a theoretical intensity or intensity ratio,, i.e., a theoretical value; a theoretical relation memory 16 for storing an existing theoretical relation of a fluorescent X-ray intensity using a plating amount and Fe% as variable parameters; a theoretical value calculator 17 for calculating a theoretical value of fluorescent X-rays by the theoretical relation while changing the parameters; and a parameter value determining circuit 18 for determining the parameters which substantially minimize a difference between the theoretical value obtained by the theoretical value converter 15 and the theoretical value obtained by the theoretical value calculator 17. These parameter values are used as a plating amount and a plating film composition to obtain the plating amount and the plating film composition of the plated steel plate to be measured. Note that the signal processor 14 may be constituted by a computer having the same functions as described above instead of the above S circuits.

An operation of the apparatus having the above arrangement will be described below. White X-rays generated from the two X-ray tubes 21 and 31 are transmitted through the collimators 22 and 32 and monochromatized by the monochromators 23 and 33, respectively. The monochromatized rays are radiated on the plated steel plate 11 at incident angles $\phi_1 = 10°$ to 30° and $\phi_2 = 45°$ to 90°. In this case, a tungsten target is used as the tube 21, and X-rays having a wavelength close to W-I$\beta$ rays having a large attenuation amount with respect to a plating film are extracted by the monochromator 23 from X-rays emitted from the tungsten target and used as incident X-rays for the plate 11. A molybdenum target is used as the tube 31, and X-rays having a wavelength close to ko-rays having a much smaller attenuation amount than that of the W-L$\beta$ rays with respect to the plating film are extracted by the monochromator 33 from X-rays emitted from the molybdenum target and used as incident X-rays for the plate 11.

After the monochromatized X-rays are radiated as described above, Kα-ray intensities of Zn and Fe generated from the plate 11 are detected by the detectors 25 and 35 at the light-receiving angles $\psi_1$ and $\psi_2$, respectively. Thereafter, $X_1$ and $X_2$ are obtained by the theoretical value converter 15 on the basis of, the fluorescent X-ray intensities or the intensity ratio obtained by the detectors 25 and 35, converted into theoretical values, and supplied to the parameter value determining circuit 18. The theoretical value calculator 17 calculates theoretical values by the existing fluorescent X-ray intensity theoretical relation stored in the theoretical value memory 16 while sequentially using the plating amount and Fe as variable parameters, and supplies the theoretical values to the parameter value determining circuit 18. The circuit 18 executes a predetermined operation by using the theoretical value supplied from the converter 15 and the theoretical value obtained by the calculator 17 by sequentially changing the parameters, determines a parameter value which minimizes a difference between the theoretical values, and obtains the plating amount and the plating film composition of the plate 11 on the basis of the parameter value.

Figure 4:
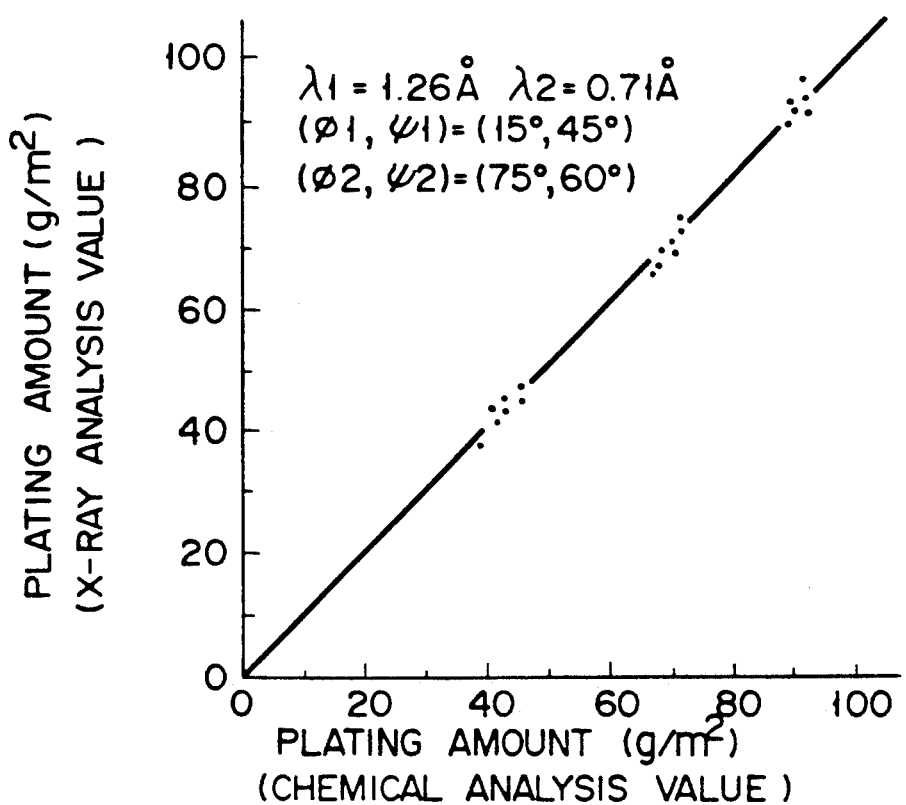
FIG. 4 is a graph showing a relationship between a plating amount obtained by the measuring method of the first aspect of the present invention and a plating amount obtained by chemical analysis.
Figure 5:
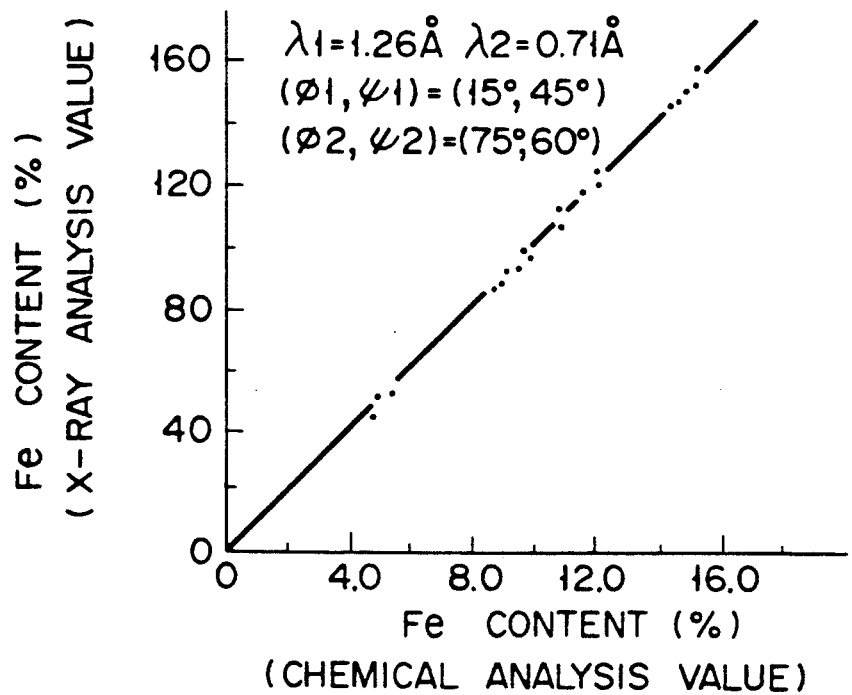
FIG. 5 is a graph showing a relationship between a plating film composition obtained by the measuring method of the first aspect of the present invention and a plating film composition obtained by chemical analysis.

FIGS. 4 and 5 are graphs showing analysis results obtained by using the apparatus shown in FIG. 3. These results are obtained by setting $\lambda_1 = 1.26$ Å and $\lambda_2 = 0.71$ Å by the monochromators 23 and 33, respectively, under the conditions of $(\phi_1, \phi_1) = (15°, 45°)$ and $(\phi_2, \psi_2) = (75°, 60°)$. FIG. 4 shows the plating amount, and FIG. 5 shows the plating film composition.

As shown in FIGS. 4 and 5, the plating amount and the Fe content obtained by the X-ray analysis according to the present invention are proportional to the plating amount and the Fe content obtained by chemical analysis, respectively. In addition, a time required for the measurement was about 10 seconds. That is, it was confirmed that the measurement can be precisely performed within a short time period though the line is a real line having a measurement distance variation, a measurement angle variation, a temperature/humidity variation, and the like.

The analysis values are obtained not directly from the fluorescent X-ray intensities of Fe and Zn but from an intensity ratio of fluorescent X-rays of Fe and Zn. Since the values are obtained by the intensity ratio, influences of the temperature/humidity variation and deterioration over time of the X-ray tube can be reduced.

FIG. 3 shows the apparatus for measuring a plating amount and a plating film composition by using a theoretical relation. An apparatus, however, may perform measurement by utilizing a calibration curve. FIG. 6 shows a signal processor of a measuring apparatus which utilizes a calibration curve. In FIG. 6, a measuring section and a drive controller are omitted because they are the same as those of the apparatus shown in FIG. 3. A signal processor 44 of this apparatus comprises: a calibration curve memory 45 for storing a calibration curve with respect to the plating amount and the plating film composition as parameters for a theoretical intensity or intensity ratio of fluorescent X-rays; and the parameter determining circuit 46 for determining the plating amount and the plating film composition which minimize a difference between an actually measured intensity or intensity ratio of fluorescent X-rays and an intensity or intensity ratio of fluorescent X-rays obtained by the calibration curve. A signal representing the fluorescent X-ray intensity or intensity ratio detected by detectors 25 and 35 and a signal from the memory 45 are supplied to the circuit 46, and the plating amount and the plating film composition which minimize a difference between the actually measured fluorescent X-ray intensity or intensity ratio and the fluorescent X-ray intensity or intensity ratio obtained by the calibration curve are determined, whether the plating amount and the plating film composition of a plated steel plate to be measured are obtained.

The second embodiment of the present invention will be described below. In this embodiment, a method is basically similar to that in the first aspect except that characteristic X-rays generated from a secondary target are used instead of monochromatized X-rays used in the embodiment. That is, in this measuring method shown in FIG. 7, characteristic X-rays $I_1$ and $I_2$ generated from two types of secondary targets are radiated on a plated steel plate 11 to be measured at incident angles $\phi_1$ and $\phi_2$ and intensities of Fkα-rays of Fe and kα-rays of Zn generated from the plate 11 are measured at light-receiving angles $\psi_1$ and $\psi_2$.

Similar to the first embodiment, this second embodiment is carried out by the flow chart shown in FIG. 2 by using the characteristic X-rays. The secondary target may be of either a reflection type or a transmission type.

Analysis results obtained by the above measuring method will be described in detail below. Assume that measurement conditions for $X_1$ are the incident X-rays $I_1$ and the measurement angles $(\phi_1, \psi_1)$ and those for $X_2$ are the incident X-rays $I_2$ and the measurement angles $(\phi_2, \psi_2)$.

In order to satisfy the condition (A) described above, a tungsten filament X-ray tube and a tungsten plate are used as an X-ray tube and the secondary target, respectively. In addition, in order to obtain the incident X-rays $I_2$ a tungsten filament X-ray tube and a molybdenum plate are used. By using these X-ray tubes and the secondary targets, smaller measurement angles $\{\phi_1 (\leq \psi_2), \Psi_1 (\leq \Psi_2)\}$ can be set to be 15° or more to satisfy the above condition (B). As a result, influences of variations in a measurement distance and a measurement angle caused by a measurement distance variation by a variation in the thickness direction of a plated steel plate can be reduced.

For the same reason as in the first embodiment the incident X-rays $I^2$ have a smaller attenuation amount with respect to a plating film than that of the incident X-rays $I^1$, and the measurement angles $(\phi_2, \psi_2)$ are larger than $(\phi_1, \phi_1)$ thereby increasing a maximum depth capable of detecting fluorescent X-rays, i.e., an analysis depth. Furthermore, in order to widen the field of view of a detector as in the first embodiment a pinhole collimator having a diameter of 2 to 5 mm is used at the incident side, and the window of a detector at the light-receiving side is opened.

In the method of the second aspect, if a large number of standard samples can be used, the standard samples may be used instead of the theoretical relation described above to obtain the plating amount and the plating film composition of the plated steel plate 11 by using a relation between a plating amount and a plating film composition, and a fluorescent X-ray intensity or intensity ratio, i.e., by using a calibration curve.

Figure 8:
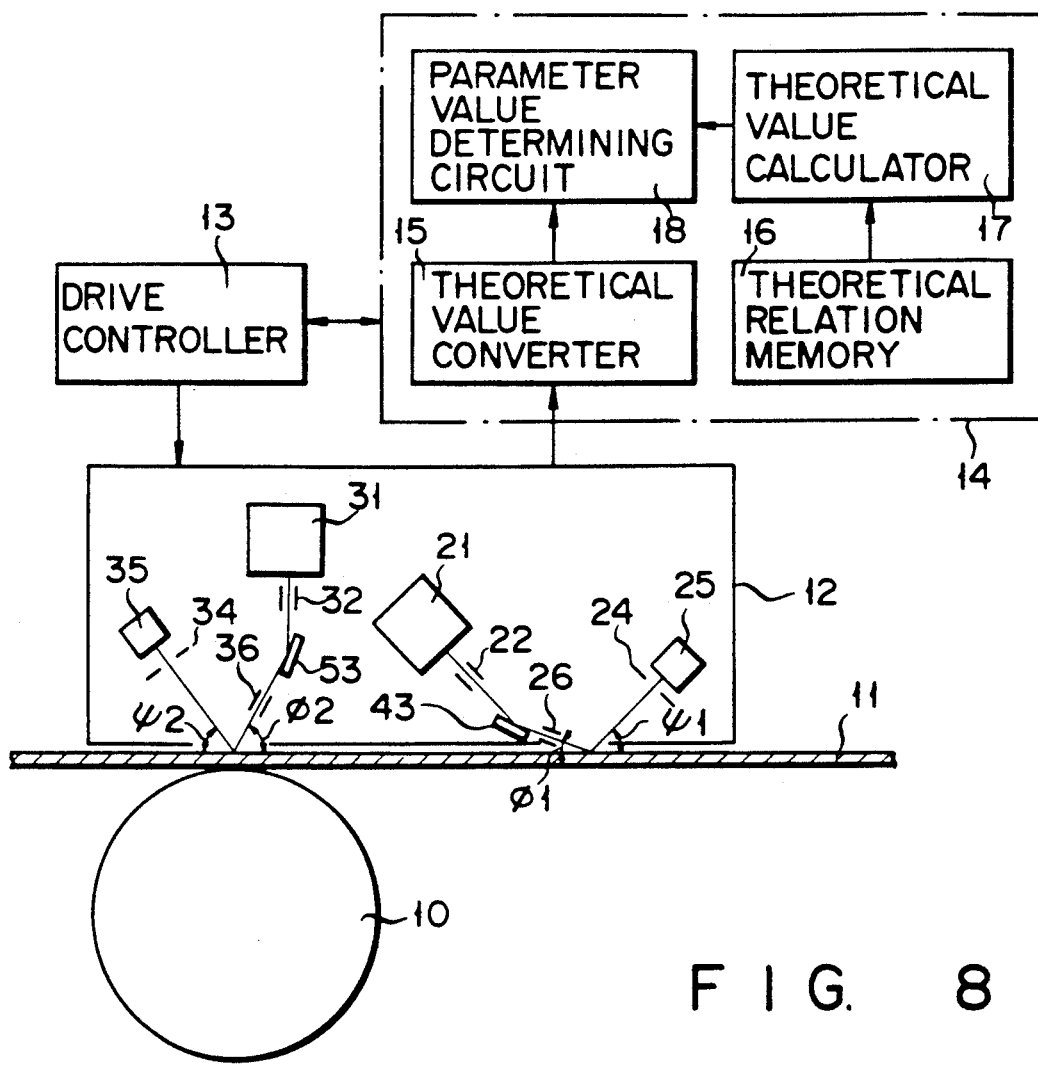
FIG. 8 is a schematic view showing an apparatus for measuring a plating amount and a plating film composition of a plated steel plate according to the second aspect of the present invention.

An embodiment of an apparatus for carrying out the second embodiment& of the present invention will be described below with reference to FIG. 8. This apparatus has the same arrangement as that of the apparatus shown in FIG. 3 for carrying out the method of the first embodiment of the present invention except that the monochromators 23 and 33 used in the first aspect are replaced by reflection secondary targets 43 and 53, respectively. In FIG. 8, the same reference numerals as in FIG. 3 denote the same parts and a detailed description thereof will be omitted In this apparatus, when white X-rays are incident on the reflection secondary targets 43 and 53 from X-ray tubes 21 and 31 through pinhole collimators 22 and 32, respectively, the targets 43 and 53 reflect and guide characteristic X-rays toward the plate 11. In the apparatus having the above arrangement, white X-rays emitted from the two X-ray tubes 21 and 31 are transmitted through the collimators 22 and 32 and incident on the targets 43 and 53, respectively, thereby generating characteristic X-rays. The characteristic X-rays generated from the targets 43 and 53 are radiated on the plate 11 at incident angles $\phi_1$ and $\phi_2$, respectively. The white X-rays emitted from the tube 21 are radiated on the target 43, and incident X-rays $I^1$ having a large attenuation amount with respect to a plating film are extracted by the target 43 and used as incident X-rays for the plate 11. The white X-rays emitted from the tube 31 are radiated o the target 53, and incident X-rays $I^2$ having a much smaller attenuation amount with respect to the plating film than that of the incident X-rays $I^1$ are extracted by the target 53 and used as incident X-rays for the plate 11.

After the incident X-rays $I^1$ and $I^2$ are radiated, Ko-ray intensities of Zn and Fe generated from the plate 11 are detected by detectors 25 and 35 at the light-receiving angles $\psi_1$ and $\psi_2$ respectively. Thereafter, parameter values are determined in the same manner as in the apparatus shown in FIG. 3, thereby obtaining the plating amount and the plating film composition of the plate 11.

Figure 9:
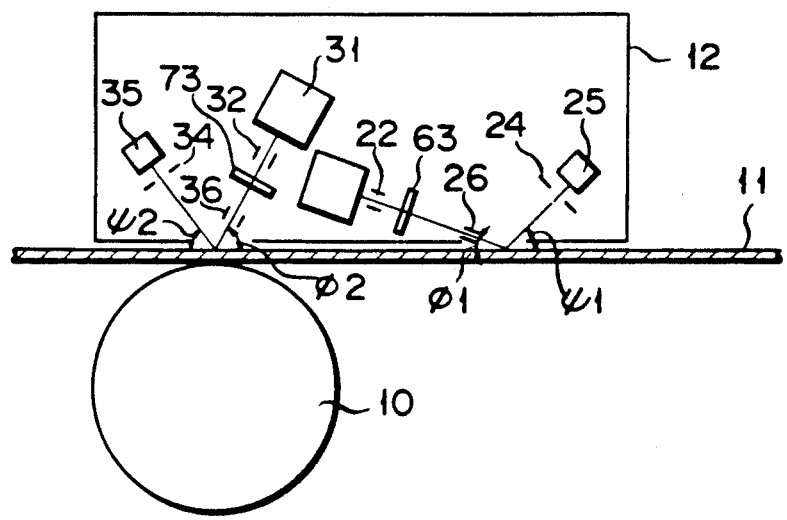
FIG. 9 is a view showing a modification of a measuring section of the apparatus shown in FIG. 8.

Note that a transmission secondary target may be used instead of the reflection secondary target. FIG. 9 is a view showing only a measuring section of an apparatus using transmission secondary targets 63 and 73 for transmitting characteristic X-rays upon X-ray radiation, instead of the reflection secondary targets 43 and 53 shown in FIG. 8. In this apparatus, a plating amount and a plating film composition can be measured in substantially the same manner as in the apparatus shown in FIG. 8.

Figure 10:
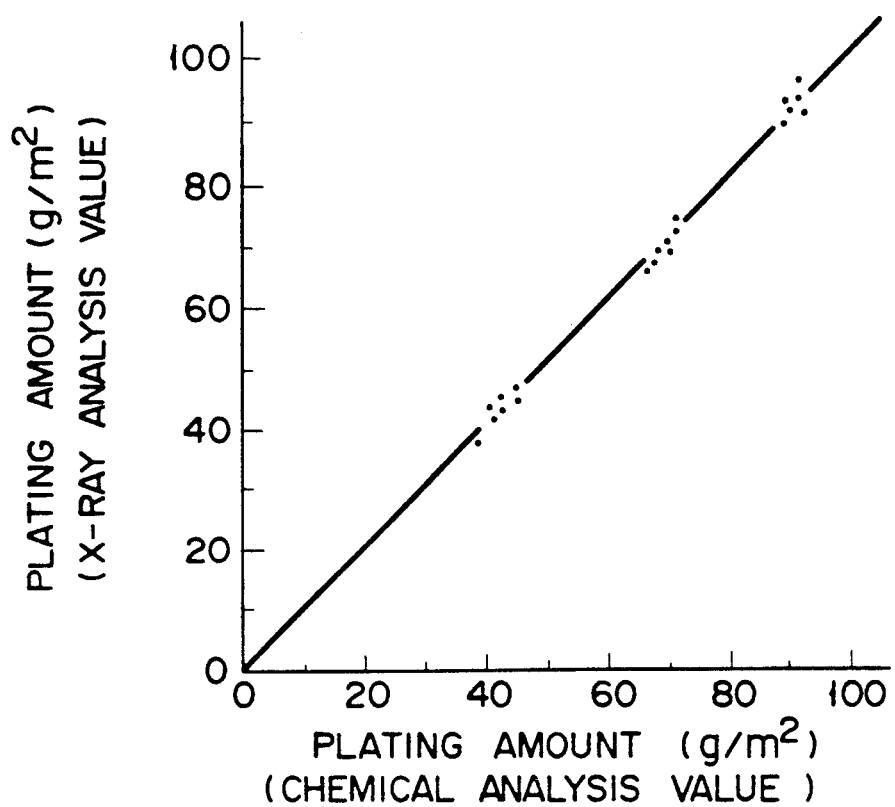
FIG. 10 is a graph showing a relationship between a plating amount obtained by a measuring method of the second aspect of the present invention and a plating amount obtained by chemical analysis.
Figure 11:
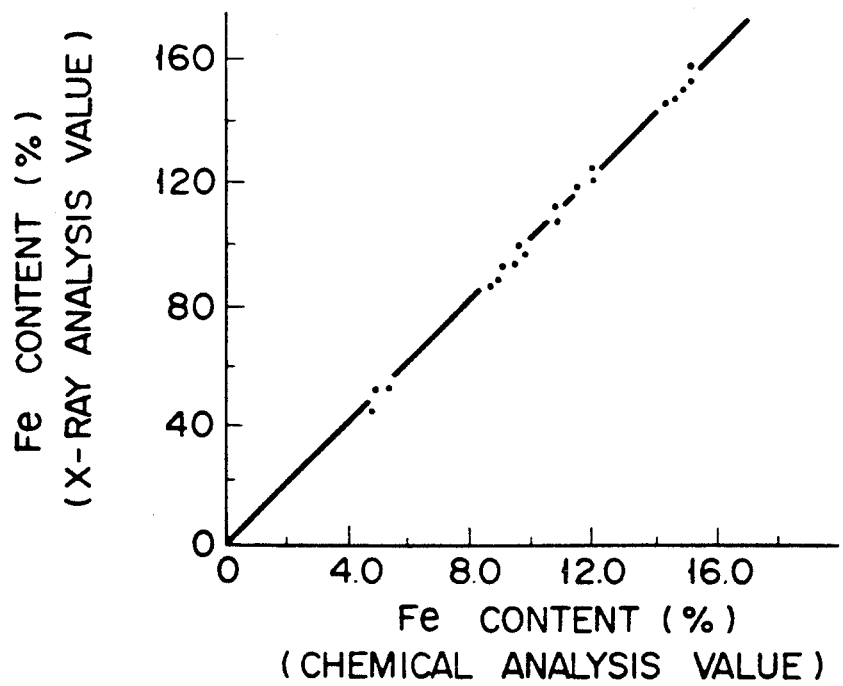
FIG. 11 is a graph showing a relationship between a plating film composition obtained by the measuring method of the second aspect of the present invention and a plating film composition obtained by chemical analysis.

FIGS. 10 and 11 are graphs showing the analysis results obtained by using the apparatus shown in FIG. 8.

As is apparent from FIGS. 10 and 11, the plating amount and the Fe content obtained by the X-ray analysis according to the present invention are proportional to the plating amount and the Fe content obtained by chemical analysis, respectively. In addition, a time required for the measurement was about 10 seconds. That is, it was confirmed that measurement can be precisely performed within a short time period though the line is a real line having a measurement distance variation, a measurement angle variation, a temperature/ humidity variation, and the like.

As in the apparatus shown in FIG. 3, in order to reduce influences of a temperature/humidity variation and deterioration over time of the X-ray tube, the analysis values are obtained not directly from the fluorescent X-ray intensities of Fe and Zn but from the fluorescent X-ray intensity ratio of Fe and Zn.

Similar to the apparatus according to the first embodiment, the apparatus according to the second embodiment may use a calibration curve instead of a theoretical relation. In this case, the same signal processor as shown in FIG. 6 described in the first aspect may be used. As a result, measurement of a plating amount and a plating film composition utilizing a calibration curve can be realized.

As has been described above, according to the methods of the present invention, X-rays having a wavelength having a large absorption amount with respect to a plating film are extracted and radiated on a plated steel plate to be measured by monochromatizing processing or a secondary target. Therefore, a fluorescent X-ray intensity can be measured at a larger measurement angle than that in a conventional apparatus. As a result, influences of a measurement distance variation and a measurement angle variation caused by a variation in the thickness direction of the plated steel plate to be measured can be reduced, and an influence of a spectral variation of incident X-rays can be reduced. In addition, since only a few types of standard samples are required in measurement to obtain conversion parameters for converting a measured value into a theoretical value, the method and apparatus of the present invention are suitable for an in-line scheme. Especially in the second aspect, no wavelength integration is required since characteristic X-rays generated from the secondary target are used as incident X-rays, thereby improving measurement precision and reducing a measurement time.

The apparatus according to the present invention can be realized with a very simple arrangement and can precisely measure the plating amount and the plating film composition of a plated steel plate to be measured by an in-line scheme. Therefore, this apparatus largely contributes to improve the quality of a plated product.

The present invention can be variously modified without departing from the spirit and scope of the invention. For examples, a two-tube system is used in FIGS. 3 and 7. Since, however, an X-ray tube generally has a plurality of X-ray extracting windows, a one-tube system can be used.

What is claimed is:

1. A method of measuring a plating amount and a plating film composition of a plated steel plate, comprising the steps of:
   (a) determining a theoretical formula for an intensity or intensity ratio at two different light-receiving angles of K-series fluorescent X-rays of analysis target elements reflected by the plated steel plate when monochromatized X-rays or characteristic X-rays are radiated onto the plated steel plate at two different incident angles;
   (b) measuring a fluorescent X-ray intensity or intensity ratio by using standard samples having known plating amounts and plating film compositions under the same conditions as for obtaining said theoretical formula, and calculating a conversion coefficient for converting the measured value into a theoretical value by said theoretical formula;
   (c) measuring a fluorescent X-ray intensity or intensity ratio obtained from a plated steel plate to be measured having unknown plating amount and plating film composition under the same conditions for obtaining said theoretical formula, and converting the measured fluorescent X-ray intensity or intensity ratio into a theoretical intensity or intensity ratio by using said conversion coefficient; and (d) calculating a plating amount and a plating film composition as parameters in the theoretical formula, which substantially minimize a difference between the theoretical intensity or intensity ratio obtained by said theoretical formula and said converted theoretical intensity or intensity ratio, as a plating amount and a plating film composition of said plated steel plate to be measured.

2. A method according to claim 1, wherein said monochromatized X-rays to be radiated on said plated steel plate are produced by a monochromator.

3. A method according to claim I, wherein said characteristic X-rays to be radiated onto said plated steel plate are obtained by radiating X-rays generated from an X-ray generator onto a secondary target.

4. A method of measuring a plating amount and a plating film composition of a plated steel plate, comprising the steps of:

(a) calculating a calibration curve of an intensity or intensity ratio at two different light-receiving angles of K-series fluorescent X-rays of analysis target elements obtained from standard samples having known plating amount and plating film composition when monochromatized X-rays or characteristic X-rays are radiated on the standard samples at two difference incident angles;

(b) measuring said fluorescent X-ray intensity or intensity ratio obtained from a plated steel plate to be measured having unknown plating amount and plating film composition under the same conditions as for obtaining said calibration curve; and (c) calculating a plating amount and a plating film composition as parameters in the calibration curve, which substantially minimize a difference between the fluorescent X-ray intensity or intensity ratio obtained by the calibration curve and said measured fluorescent X-ray intensity or intensity ratio, as a plating amount and a plating film composition of said plated steel plate to be measured.

5. A method according to claim 4, wherein the monochromatized X-rays to be radiated onto said plated steel plate are produced by a monochromator.

6. A method according to claim 4, wherein the characteristic X-rays to be radiated onto said plated steel plate are obtained by radiating X-rays generated from an X-ray generator onto a secondary target.

7. An apparatus for measuring a plating amount and a plating film composition of a plated steel plate, comprising:

X-ray generating means for generating X-rays;
converting means for converting X-rays generated by said X-ray generating means into monochromatic X-rays or characteristic X-rays;
a pair of detectors for receiving, at two different angles, K-series fluorescent X-rays of analysis target elements generated when said monochromatic X-rays or characteristic X-rays are radiated onto a plated steel plate to be measured, and measuring the intensities thereof;
a slit system for guiding X-rays generated by said X-ray generating means to pair of detectors via said converting means and said plating steel plate to be measured;
storage means for storing a theoretical formula used to calculated a theoretic intensity or intensity ratio of fluorescent X-rays to be obtained in a given measurement system, said theoretic formula using a plating amount and a plating composition of a plated steel plate as parameters;
theoretical value calculating means for calculating a theoretical value of the fluorescent X-ray intensity or intensity ratio by said stored theoretical formula while changing said parameters;
theoretic value converting means for converting an actually measured fluorescent X-ray intensity or intensity ratio into a theoretical intensity or intensity ratio; and
plating amount/plating film composition determining means for determining a plating amount and a plating film composition as said parameters, which substantially minimize a difference between the converted theoretical intensity or intensity ratio and the theoretical intensity or intensity ratio obtained by said theoretical formula.

8. An apparatus according to claim 7, wherein said converting means has a monochromator for monochromatizing X-rays generated from said X-ray generating means.

9. An apparatus according to claim 7, wherein said converting means has a reflection secondary target for reflecting characteristic X-rays generated by said X-ray generating means.

10. An apparatus according to claim 7, wherein said converting means has a transmission secondary target for transmitting characteristic X-rays generated by said X-ray generating means.

11. An apparatus according to claim 7, wherein said slit system has a collimator located at an incident side and a flat-plate slit located at a light-receiving side and having a variable width.

12. An apparatus according to claim 11, wherein said collimator is a pinhole collimator.

13. An apparatus for measuring a plating amount and a plating film composition of a plated steel plate, comprising:

X-ray generating means for generating X-rays;
converting means for converting X-rays generated by said X-ray generating means into monochromatic X-rays or characteristic X-rays;
a pair of detectors for receiving, at two different angles, K-series fluorescent X-rays of analysis target elements generated when said monochromatic X-rays or characteristic X-rays are radiated onto a plated steel plate to be measured, and measuring the intensities thereof;
a slit system for guiding X-rays generated by said X-ray generating means to said pair of detectors via said converting means and said plated steel plate to be measured;
storage means for storing a calibration curve of a theoretical intensity or intensity ratio of fluorescent X-rays to be obtained in a given measurement system with respect to a plating amount and a plating film composition of a plated steel plate; and
plating amount/plating film composition determining means for determining a plating amount and a plating film composition which substantially minimize a difference between an actually measured fluorescent X-ray intensity or intensity ratio and a fluorescent X-ray intensity or intensity ratio obtained by the calibration curve.

14. An apparatus according to claim 13, wherein said converting means has a monochromator for monochromatizing X-rays generated by said X-ray generating means.

15. An apparatus according to claim 13, wherein said converting means has a reflection secondary target for reflecting characteristic X-rays generated by said X-ray generating means.

16. An apparatus according to claim 13, wherein said converting means has a transmission secondary target for transmitting characteristic X-rays generated by said X-ray generating means.

17. An apparatus according to claim 13, wherein said slit system has a collimator located at an incident side and a flat-plate slit located at a light-receiving side and having a variable width.

18. An apparatus according to claim 17, wherein said collimator is a pinhole collimator.

19. An apparatus according to claim 7, wherein said theoretical value converting means converts said actually measured fluorescent X-ray intensity or intensity ratio into a theoretical intensity or intensity ratio according to converting equations which have converting parameters defined by a relationship between said theoretical formula and fluorescent X-ray intensities or intensity ratios measured from standard samples having know plating amounts and plating film compositions.

* * * * *

UNITED STATES PATENT AND TRADEMARK OFFICE
CERTIFICATE OF CORRECTION

PATENT NO. : 5,081,658
DATED : January 14, 1992
INVENTOR(S) : IMAI et al It is certified that error appears in the above-identified patent and that said Letters Patent is hereby corrected as shown below:

Title page, in Section [56] References Cited, under "FOREIGN PATENT DOCUMENTS", list the following:

```
0,072,367  2/1983    European Patent Office
2-302654   12/1990   Japan*
59-225312  12/1984   Japan*
61-195335  8/1986    Japan*         * Abstracts only.
```

"OTHER DOCUMENTS" :

Patent Abstracts of Japan, April 11, 1984, Vol.8, No.79

Signed and Sealed this

Twenty-first Day of December, 1993

*Attest:*

BRUCE LEHMAN

*Attesting Officer*     *Commissioner of Patents and Trademarks*